United States Patent
Begemann

(10) Patent No.: US 6,526,311 B2
(45) Date of Patent: Feb. 25, 2003

(54) SYSTEM AND METHOD FOR SENSING AND DETECTING FAR-FIELD R-WAVE

(75) Inventor: Malcolm J. Begemann, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/916,457

(22) Filed: Jul. 30, 2001

(65) Prior Publication Data

US 2002/0040191 A1 Apr. 4, 2002

Related U.S. Application Data

(60) Provisional application No. 60/225,037, filed on Aug. 11, 2000.

(51) Int. Cl.$^7$ ................................................. A61B 5/04
(52) U.S. Cl. ....................................................... 600/509
(58) Field of Search .................................. 600/509, 521

(56) References Cited

U.S. PATENT DOCUMENTS

| | | | |
|---|---|---|---|
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallok |
| 4,800,883 A | 1/1989 | Winstrom |
| 4,821,723 A | 4/1989 | Baker, Jr. et al. |
| 4,830,006 A | 5/1989 | Haluska et al. |
| 4,880,005 A | 11/1989 | Pless et al. |
| 4,949,719 A | 8/1990 | Pless et al. |
| 4,953,551 A | 9/1990 | Mehra et al. |
| 5,099,838 A | 3/1992 | Bardy |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,269,298 A | 12/1993 | Adams et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,545,186 A | 8/1996 | Olson et al. |
| 5,941,906 A | 8/1999 | Barreras, Sr. et al. |

FOREIGN PATENT DOCUMENTS

| WO | WO92/18198 | 10/1992 |
|---|---|---|

OTHER PUBLICATIONS

Olson et al. "Onset and Stability for Ventricular Tachyarrhythmia Detection in an Implantable Pacer–Cardioverter–Defibrillator" Computers in Cardiology, Oct. 7–10, 1986, IEEE Computer Society Press, p. 167–170.

Arzbaecher et al. "Automatic Tachycardia Recognition" PACE May/Jun. 1984, p. 541–547.

*Primary Examiner*—Mark Bockelman
(74) *Attorney, Agent, or Firm*—Thomas F. Woods; Eric R. Waldkoetter; Tom G. Berry

(57) ABSTRACT

An improved system and method for analyzing far-filed R-waves detected by a sensing device located in the atrium of a patient's heart are provided.

5 Claims, 7 Drawing Sheets

SYSTEM AND METHOD FOR SENSING AND DETECTING FAR-FIELD R-WAVE

RELATED APPLICATIONS

This patent application claims priority and other benefits from U.S. Provisional Patent Application Ser. No. 60/225,037 entitled "System and Method for Detection Far-Field R-Wave Sensing" to Begemann filed Aug. 11, 2000, and incorporates the entirety of same by reference herein.

FIELD OF THE INVENTION

This invention is generally directed to the field of implantable pacemakers defibrillators, and methods of delivering therapies using same.

SUMMARY OF THE INVENTION

An improved system and method for analyzing far-filed R-waves detected by a sensing device located in the atrium of a patient's heart are provided,

BRIEF DESCRIPTION OF THE DRAWINGS

The present invention will become better understood by reference to the following Detailed Description of the Preferred Embodiments of the present invention when considered in connection with the accompanying Figures, in which like numbers designate like parts throughout, and where.

DETAILED DESCRIPTION OF THE INVENTION

Figure 1:
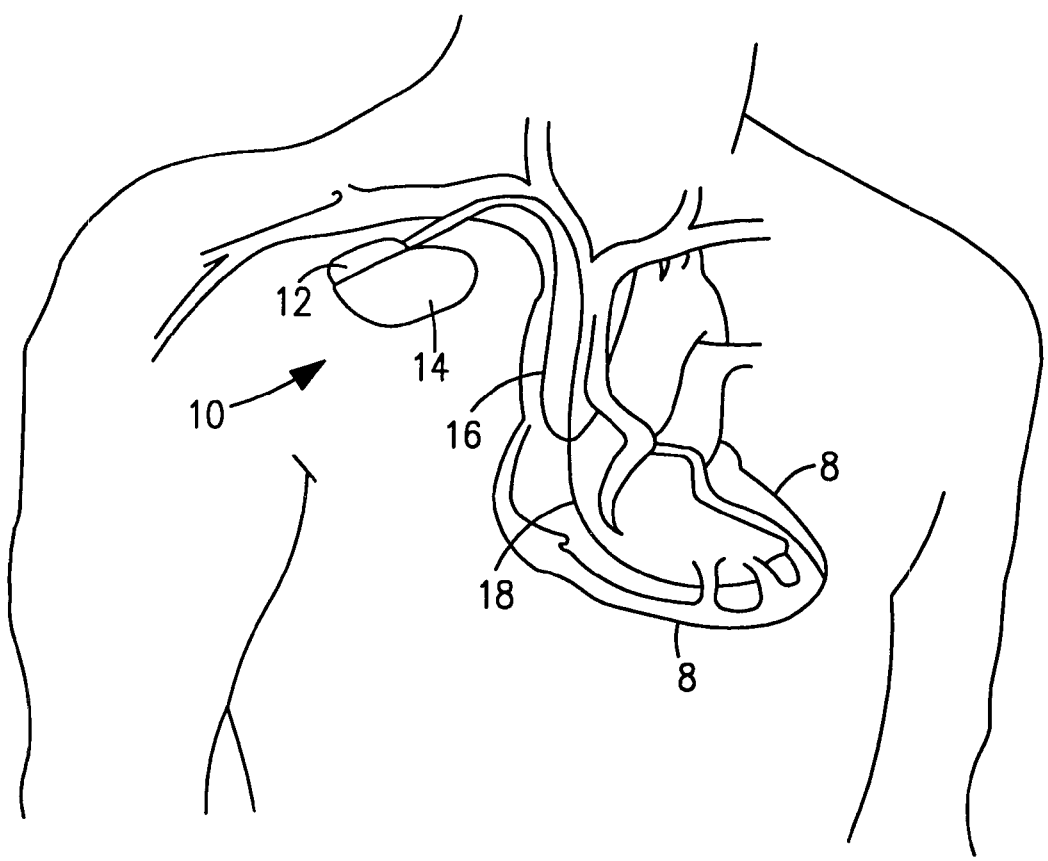
FIG. 1 shows a simplified schematic view of one embodiment of an IMD that may be employed in conjunction with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
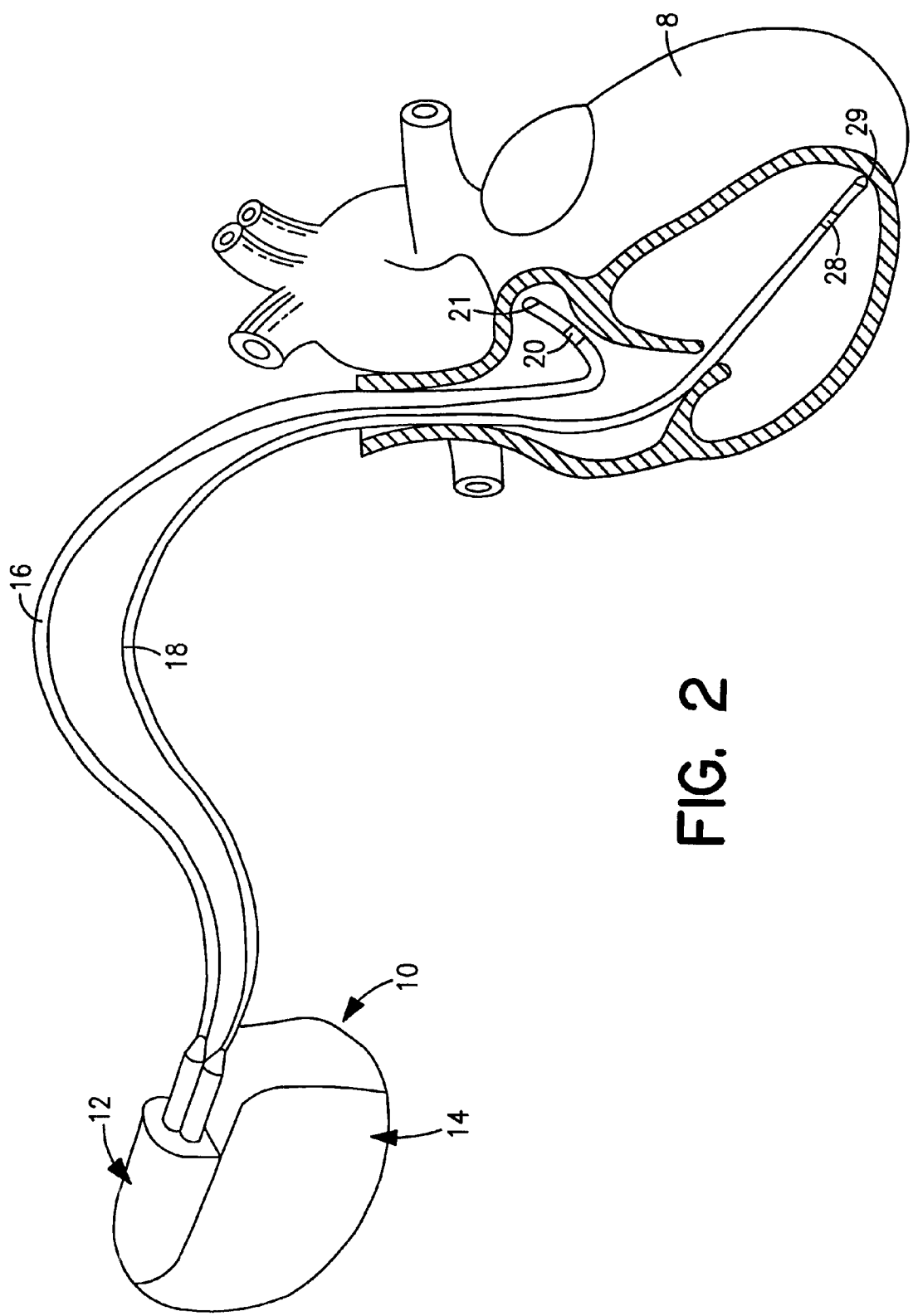
FIG. 2 shows a simplified illustration of an IMD with medical electrical leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
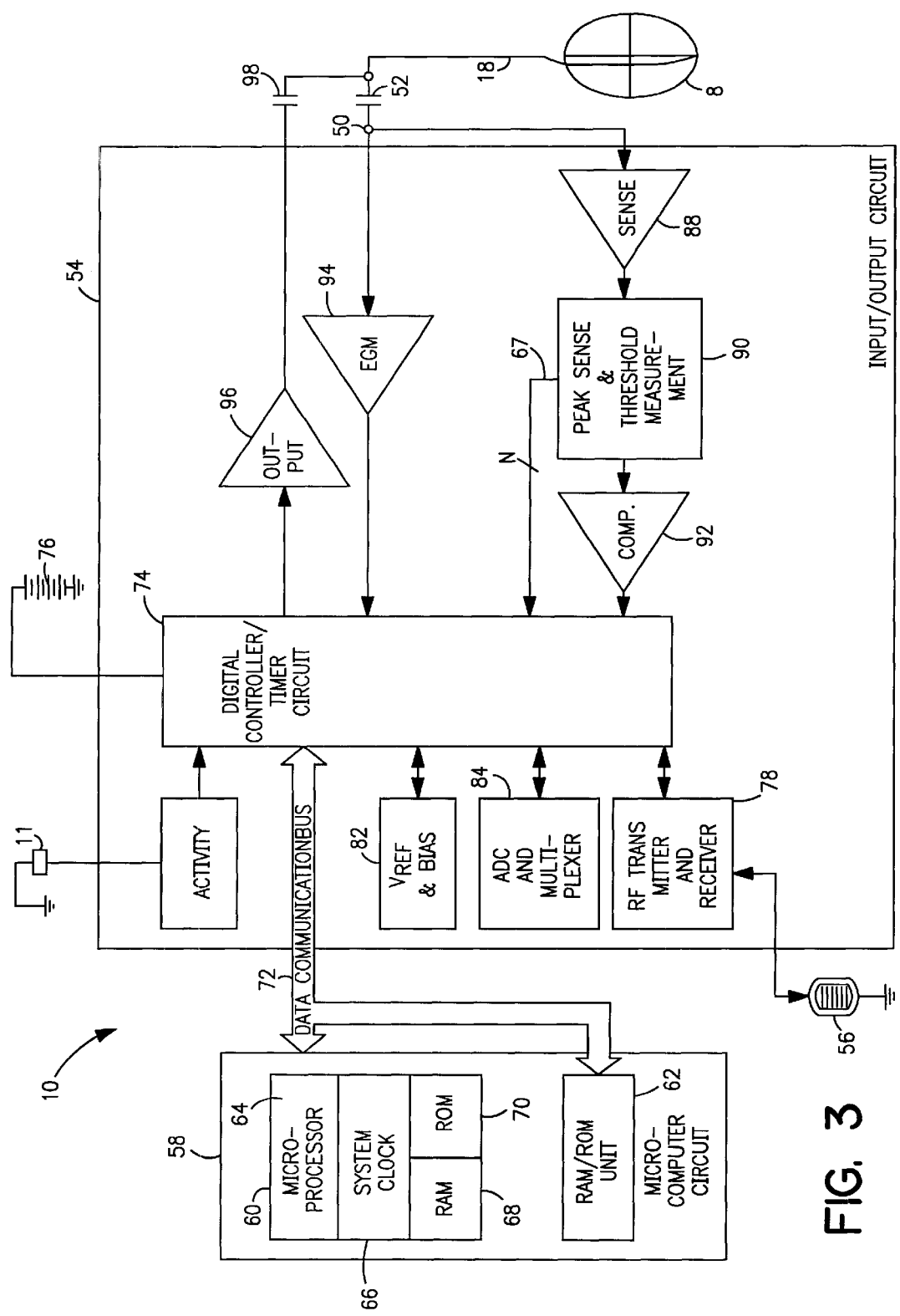
FIG. 3 shows a block diagram illustrating some constituent components of an IMD.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programing unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirely. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/ downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred tit the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement fictions. Operating commands for controlling the ting of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At let some embodiments of the present invention may be applied equally well in the contexts of single, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
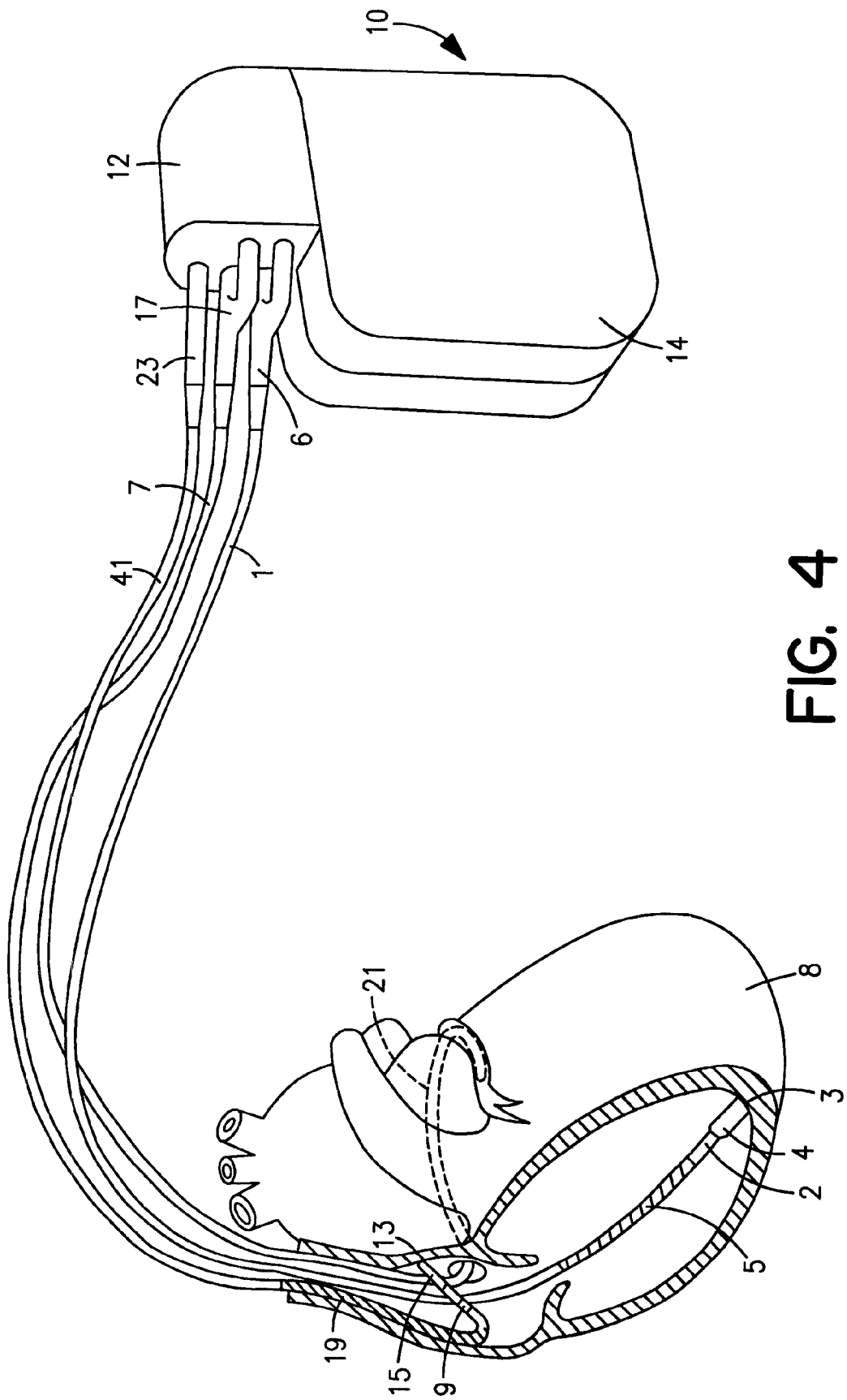
FIG. 4 shows a simplified schematic view of an IMD with medical electrical leads positioned within passageways of a heart.
Figure 5:
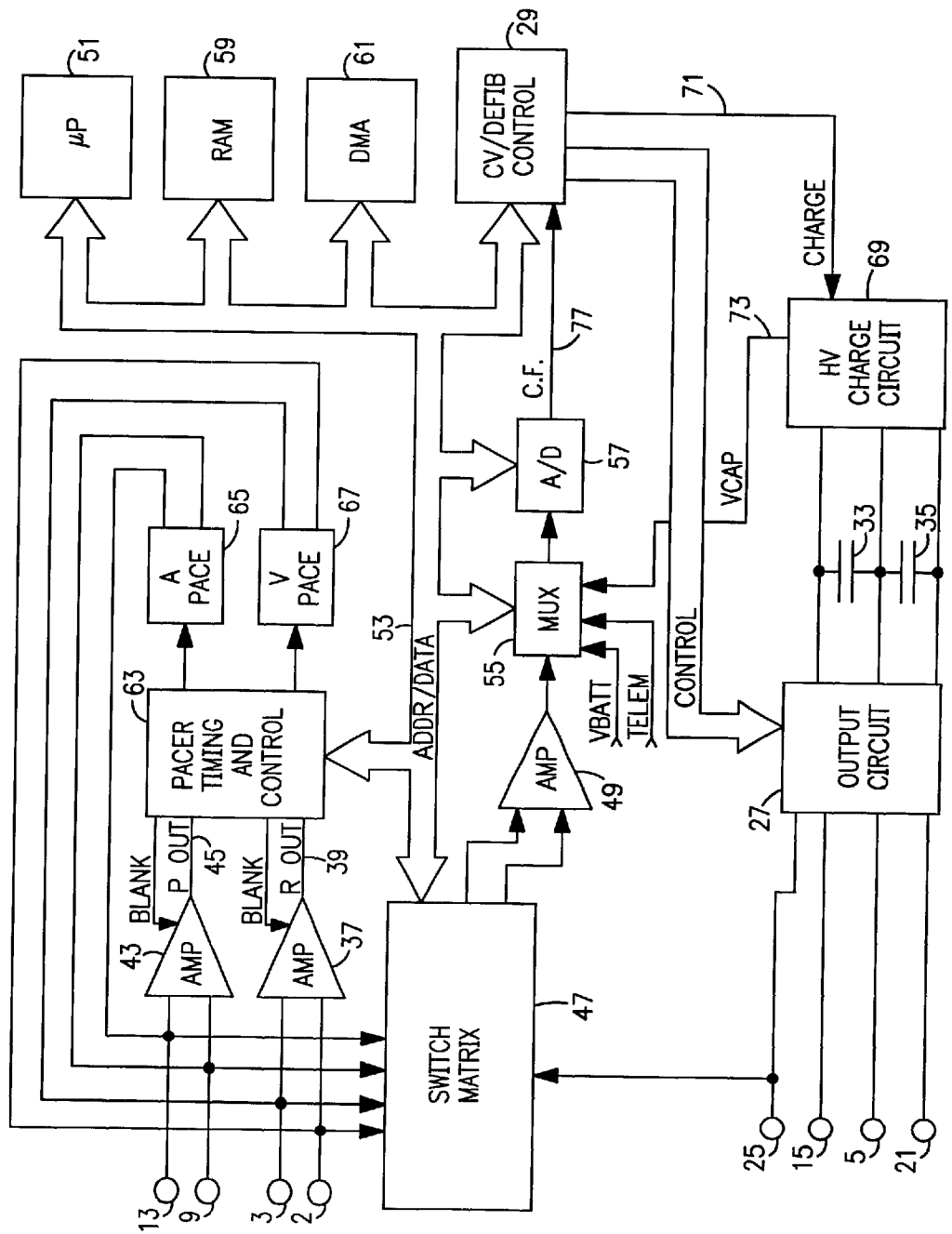
FIG. 5 shows a partial block diagram illustrating one embodiment of an IMD that may be employed in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals front the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when react by sensed R-waves and P-waves may be used to measure the durations of R-R intervals, P-P intervals, P-R intervals and R-P intervals, which measurements are stored in memory 59 and used to detect the presence of tachyanhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in tie art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application U.S. Ser. No. 92/02829, Publication No. WO92/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer tiring and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which arc incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 ad 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 21 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Turning now to the on-chip capacitor aspect of the present invention, we note at the outset that capacitors 76, 98 and 52 of FIG. 3, typically deployed as discrete capacitors wire bonded to an IC, as well as other capacitors, are well suited for adaptation as on-chip deep trench capacitors of the present invention. We note further that programmed voltage storage capacitors C1, C2, C3 and C4 in Output Mux 48 shown in FIG. 2 of U.S. Pat. No 5,941,906 are also well suited for adaptation as on-chip deep trench capacitors of the present invention.

Although specific embodiments of the invention are described here in some detail, it is to be understood that those specific embodiments are presented for the purpose of illustration, and are not to be taken as somehow limiting the scope of the invention defined in the appended claims to those specific embodiments. It is also to be understood that various alterations, substitutions, and modifications may be made to the particular embodiments of the present invention described herein without departing from the spirit and scope of the appended claims.

All printed publications, patents and patent applications referenced hereinabove are hereby incorporated by referenced herein, each in its respective entirety.

This invention relates to a system and method for detecting the sensing of far field R waves in the atrium. Far field R waves involve ventricular events that are sensed by a sensor located within the atrium. If these sensed far-field R-waves are incorrectly classified as atrial beats, rate responsive pacing may not function properly. Therefore a system is needed to correctly classify far field R waves so that these sensed signals are not classified as atrial events.

The current invention is an improved system and method for analyzing far field R waves detected by a sensing device located with the atrium. According to one embodiment of the invention, the following criteria is used to determine if a sensed signal in the atrium is a far-field R wave:

1. A time between a ventricular sensed event and the following atrial sensed event is smaller than a selected V A interval. This selected V A interval is also referred to as FFRAmax.

2. The difference in time from the previous atrial sense (Ap) to the current atrial sense (A), and the difference in time from the current atrial sense (A) to the following atrial sense (Af) is smaller than some predetermined variability. This variability is referred to as Aaf/ApA.

3. No 1:2 block occurred, and half of the interval between the previous atrial sense (Ap) and the current atrial sense (A) exceeds the post-ventricular atrial blanking period (PVAB).

4. The number of atrial senses within a selected window (delta VA) is higher than the number of possible far-field R-waves (#FF).

If all of the conditions above are met, far-field R-waves are detected.

It will be noted that each of the criteria includes a variable parameter that must be selected. This includes FFRAmax, AAf/ApA, PVAB, and #FF. Table 1 summarizes the various variables that are used in the current system and method.

According to one embodiment of the invention, at least some of these parameters are selected when a user selects a confidence level, which is a value between 0 and 100 percent. That is, the user selects a single confidence level, which the system automatically translates into a percentage value for AAf/ApA, a time value for delta VA, and a positive integer value for #FF. The various values used in one embodiment of the current invention for a selected confidence level are shown in Table 2. Alternatively, the user may select a value for one of the variables such as AAf/ApA, and the other variables will be adjusted appropriately.

The variable FFRAmax has no influence on the confidence level. The range of this parameter is between 0 and 250 ms, with the default value being 180 ms.

Figure 6:
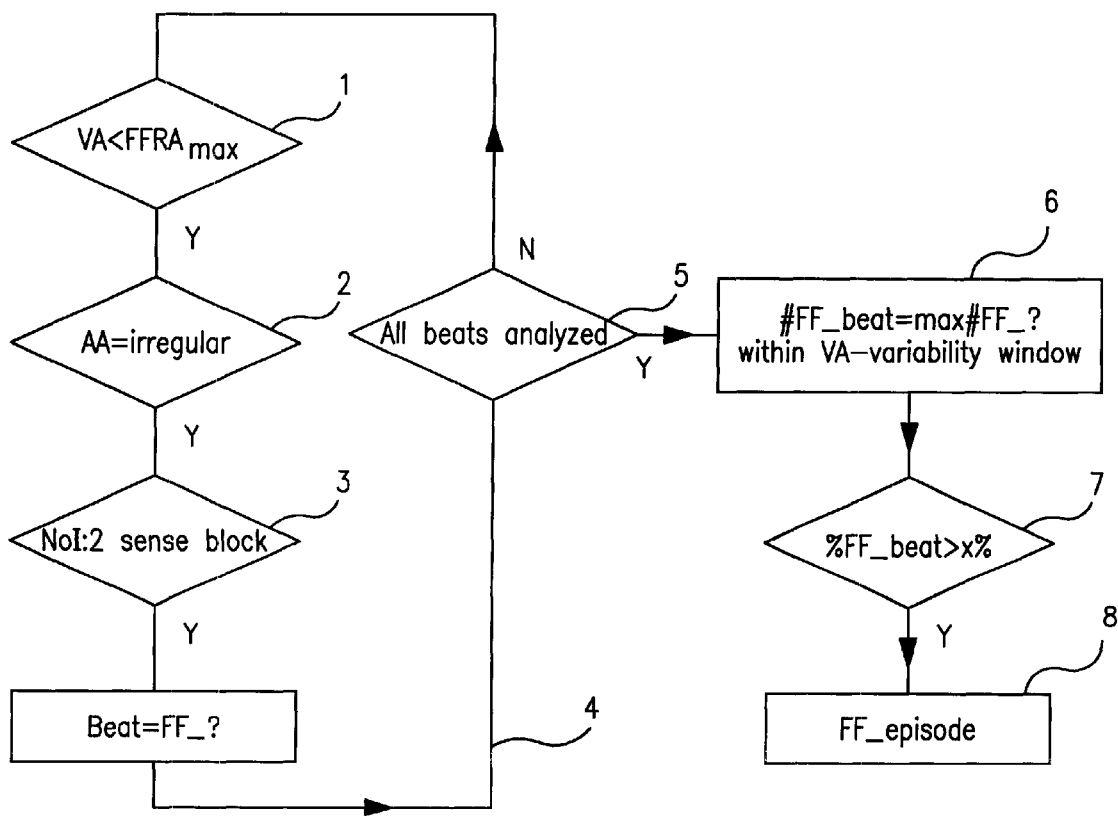
FIG. 6 shows a flow chart according to one method of the present invention.

FIG. 6 is a flowchart describing the method for using the above-described parameters to detect far field R wave sensing. In step 1, it is determined whether tie current VA length is less than the selected value for FFRAmax. If so, it is determined whether AA is irregular in step 2. The AA time is said to be irregular if the current AA time multiplied by the factor (1+AAf/ApA) is less than the AA time from the current atrial sense to the next atrial sense. If the AA time is irregular in step 2, a check is made for 1:2 block, as shown in step 3. If no such block is occurring, then the atrial sense is designated as a potential far-field R wave sense. These steps are repeated for all atrial senses, as shown by arrow 4.

When all beats are analyzed, as shown in step 5, the potential far-field R wave senses are analyzed further. These events are sorted by VA time in time-increasing order. Next, a check is performed for an interval in the series of VA times, wherein the sum of counts of marked events inside the interval is maximal. The range of the interval is half of delta VA to the left, and half of delta VA to the right. It is then determined whether the count of marked events inside the interval is greater than #FF. If this count of marked events is greater than #FF as shown in step 7, far-fields are detected at the selected confidence level as shown in step 8. Further examples of these calculations are shown in Example 1.

Figure 7:
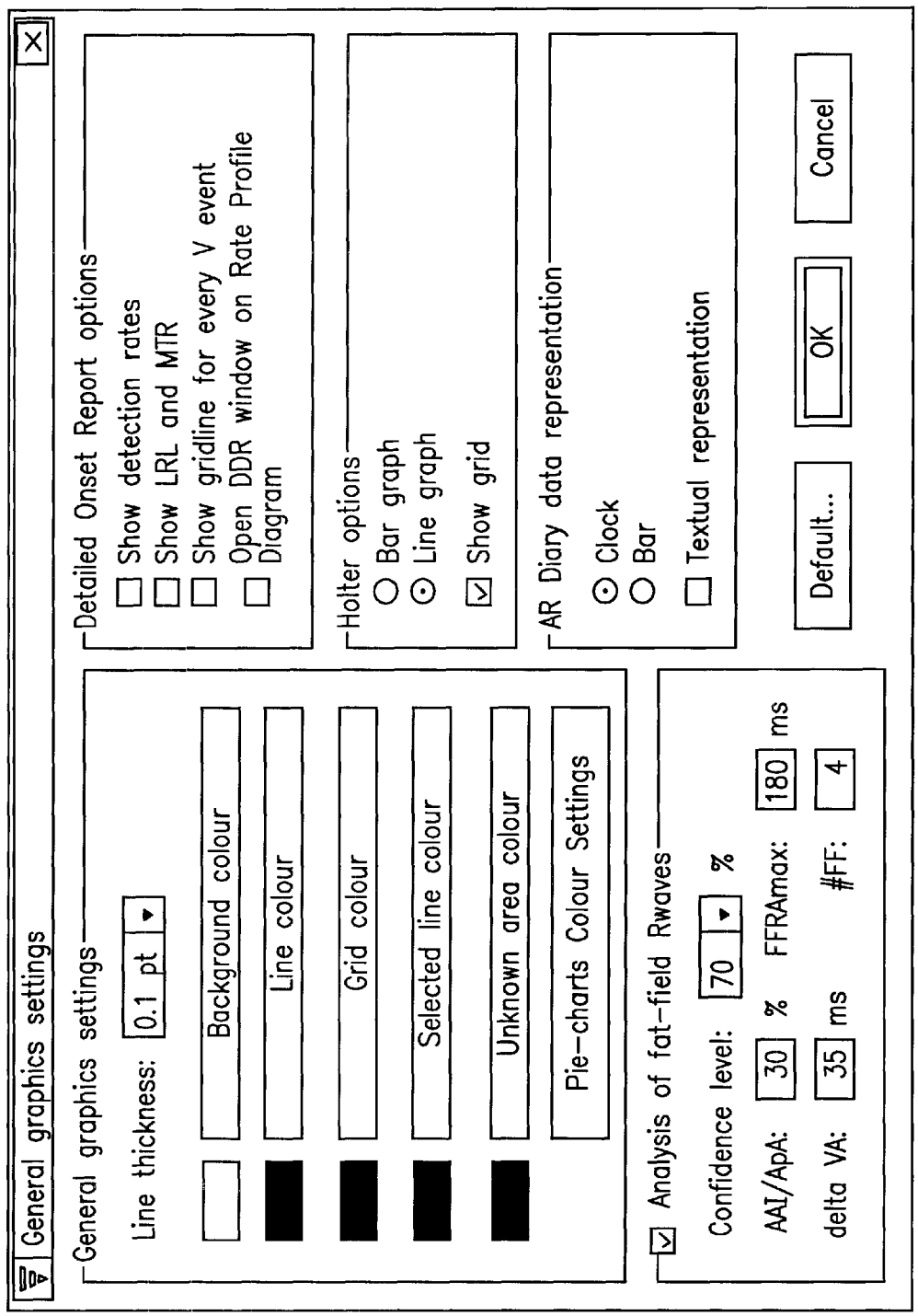
FIG. 7 shows an example of a user interface in accordance with one embodiment of the present invention.

In one embodiment of the invention, selecting the confidence is performed using a user interface as shown in FIG. 7. The variables for analyzing far field R waves are entered in the lower left-hand corner of the screen. In general, FFRAmax may be left to the default value of 180 ms, or set to another value between 0 and 250 ms. The other variables may be selected by entering a single one of these other variables in the manner discussed above. The system will automatically select the rest of the variables. If far-field Rwave senses are detected the "FFR" label is displayed in the DOR list and a warning will be placed in the header of the of a rate profile diagram and the marker ECG diagram.

The current invention may be employed by an implantable device having sensing and/or pacing capabilities, and may also be employed by an external device having sensing capabilities. A user interfaces such as that shown in FIG. 2 may be provided by a programmer or other type of user display provided by a sensing device.

Analysis of Far-Field R-Waves

The analysis of far-field R-waves can be selected in the properties window (see FIG. 7). Upon selecting this option, a message appears informing you that this function is included for investigational purposes only. The far-field R-wave analysis examines all interrogated detailed onset reports for the presence of far-field R-waves.

The confidence level of this analysis is a function of:
the AA variability (AAf/ApA);
the VA variability (delta VA);
the number of possible far-field R-waves (#FF) within the VA variability window.

You can select one of the preset confidence levels in the properties window. This will set the other parameters to their corresponding values. Atrial sensed beats are classified as far-field R-waves if:

1. The current VA interval is smaller than the maximum VA interval (FFRAmax).

2. The AA interval is irregular: that is, the difference in time from the previous (Ap) to the current (A) atrial sense and from the current (A) to the following (Af) atrial sense is smaller than the AA variability (AAf/ApA).

3. There is no 1:2 block: therefore, half of the interval between the previous (Ap) and the current (A) atrial sense (½ ApA) exceeds the post-ventricular atrial blanking period (PVAB).

4. The number of atrial senses found within the VA variability window (delta VA) is higher than the number of possible far-field R-waves (#FF).

If all these conditions are met, far-field R-waves are detected at the selected confidence level.

In the main window, the detailed onset reports for which far-field R-waves are detected will be marked with 'FFR', and in the header of the rate profile and marker ECG diagrams a warning is displayed.

Description of algorithm for Far Field R-waves sensing analysis. Far Field R-waves sensing analysis is executed only if it is selected in the Properties Window, after which the following warning appears: "This analysis examines all interrogated detailed onset reports for the presence of far-field R-waves, based on a timing model. It has not been evaluated on accuracy sensitivity and specificity have not yet been demonstrated." The analysis is executed for all interrogated Detailed Onset Reports. The algorithm for the Far-field R-wave sensing analysis uses the following values (r=the report number from 0 to 15).

TABLE 1

VARIABLE FOR FFR ANALYSIS

| name of parameter | units | description |
|---|---|---|
| Event type | | type of event, line Y110 + r*15 in Vitatron Save To Disk file |
| AA | ms | time from atrial event to next atrial event, line Y111 + r*15 in Vitatron Save To Disk file |
| VA | Ms | time from ventricular event to next atrial event, line Y112 + r*15 in Vitatron Save to Disk file |
| AAf/ApA | % | coefficient of AA between following and previous events, to set in Properties Window |
| Delta VA | Ms | width of interval in series of VA times, to set in Properties Window |
| #FF | 1 | count of possible far-fields in interval determined by detla VA |
| FFRAmax | Ms | VA time limit for the first criterion |

The analysis proceeds in four steps:

1. Step. Looking for possible far fields. All atrial events (Event type: AS, TAS, PAC, RAS, AP, ASP) are tested for following criteria:

VA(current event)<FFRAmax

AA(current event)*(1+AAf/ApA)<AA (following atrial event)

If this event fits to this criterion, check it for 1:2 block. If no 1:2 block is detected, then mark this event as a possible far-field R-wave sense.

2. Step. Sort marked events by VA time in increasing order.

3. Step. Look for interval in series of VA times, where sum of counts of marked events inside interval is maximal. Range of interval is half of delta VA to left and half of delta VA to right.

4. Step. If count of marked events inside interval (from step 3) is bigger than #FF, far-fields are detected at the selected Confidence level.

The Confidence level is a function of AAf/ApA, delta VA and #FF. The user can select one of the preset values of the Confidence level, which will change the other three parameters to their corresponding values. The table below shows the preset values.

TABLE 2

| FFR analysis parameter values | | | | | | |
|---|---|---|---|---|---|---|
| Confidence level | <0%; 100%> | 50% | 70% | 75% | 90% | 95% |
| AAf/ApA | <0%; 100%> | 20% | 30% | 30% | 40% | 40% |
| Delta VA | <0 ms; 999 ms> | 50 ms | 35 ms | 35 ms | 20 ms | 20 ms |
| #FF | <0; 10> | 4 | 4 | 8 | 4 | 8 |

The parameter FFRAmax has no influence on the confidence level, Its range is <0 ms; 250 ms>, and its default value is 180 ms.

If far-field R-wave senses are detected for some Detailed Onset Report, the MFFRM label is displayed for this report in the DOR list and the warning "WARNING: Possible Far Field R-Wave sensing. Confidence level: xx %" is placed in the header of the Rate Profile Diagram and the Marker ECG Diagram.

EXAMPLE1

AA=irregular is determined by comparing the interval from the previous A-sense with the interval to the next A-sense. If the difference is larger than a determined percentage (or for patent sake larger than constant), then AA is determined irregular No 1:2 sense block is determined by subtracting half of the interval from the previous A-sense from the time of this A-sense and calculate if the resulting time falls in the A-refractory (or blanking) period, with a certain margin.

All beats analysed is only valid for a "post hock" analysis of our detailed onset recordings where a CE number of beats are stored For a "real time" operation, the calculation can be performed on a continous basis.

FF_beat=max #FF_? within VA-variability window is a more complicated one and best explained by an example: If the VA-variability window is 50 ms, the algorithm calculates how many FF_? beats fall in the VA-range 0 to 50 ms, 10 to 50 ms, 20 to 70 ms, 30 to 80 ms etc. The highest number of all these VA-ranges is taken (for instance if 7 FF_? beats fell In the range 50 to 100 ms and was less in all other ranges, the number of 7 is taken (and the corresponding VA time for the FF beats derived as 75 ms plus or minus 25). %FF_beat>x%%FF_boat is #FF_beat as a percentage of the total number of beats. I think we take the number of V_beats, but A-beats could also be taken.

What is claimed is:

1. A method for detecting cardiac far-field R-waves using an implatable medical device, comprising:

sensing a ventricular event or pacing the ventricular event;

recording atrial events including at least a past atrial event, a current atrial event, and a next atrial event;

measuring a first time interval between the ventricular event and the current atrial event;

measuring a second time interval between the past atrial event and the current atrial event;

measuring a third time interval between the current atrial event and the next atrial event;

calculating whether the first time interval is less than a predetermined first time interval amount;

determining a first criteria for potential far-field R-waves if the first time interval is less than the predetermined first time interval amount;

calculating whether the second time interval differs from the third time interval by a predetermined interval amount;

determining a second criteria for potential far-field R-waves is met if the second time interval differs from the third time interval by the predetermined interval amount;

calculating the number of first time intervals that are substantially constant in duration;

determining a third criteria for potential far-field R-waves is met if there are at least two substantially constant first time intervals; and, deciding that there are far-field R-waves if the first criteria, second criteria, and third criteria are met.

2. The method as in claim 1, further comprising, calculating whether the second time interval midpoint occurs within a post-ventricular atrial blanking period;

determining a fourth criteria for potential far-field R-waves is met if the second time interval midpoint does not occur within the post-ventricular atrial blanking period; and, deciding that there are far-field R-waves if the first criteria, second criteria, third criteria, and fourth criteria are met.

3. The method as in claim 1, wherein the predetermined first time interval amount is adjusted once far-field R-waves are confirmed.

4. The method as in claim 1, wherein once the third criteria for potential far-field R-waves is met, additional first time intervals fulfilling the first criteria and the second criteria will be determined to be far-field R-waves if the additional time intervals are substantially the same as the at least two substantially constant first time intervals.

5. The method as in claim 1, wherein the first time interval predetermined amount is adjusted once far-field R-waves are confirmed.

* * * * *